(12) United States Patent
Wang et al.

(10) Patent No.: US 11,344,272 B2
(45) Date of Patent: May 31, 2022

(54) DEVICE AND METHOD FOR COMPUTER-AIDED DIAGNOSIS BASED ON IMAGE

(71) Applicant: Ping An Technology (Shenzhen) Co., Ltd., Shenzhen (CN)

(72) Inventors: Yirui Wang, Bethesda, MD (US); Haomin Chen, Bethesda, MD (US); Kang Zheng, Bethesda, MD (US); Adam Harrison, Bethesda, MD (US); Le Lu, Bethesda, MD (US); Shun Miao, Bethesda, MD (US)

(73) Assignee: Ping An Technology (Shenzhen) Co., Ltd., Shenzhen (CN)

( * ) Notice: Subject to any disclaimer, the term of this patent is extended or adjusted under 35 U.S.C. 154(b) by 306 days.

(21) Appl. No.: 16/850,622

(22) Filed: Apr. 16, 2020

(65) Prior Publication Data

US 2021/0212651 A1 Jul. 15, 2021

Related U.S. Application Data

(60) Provisional application No. 62/958,965, filed on Jan. 9, 2020.

(51) Int. Cl.
*A61B 6/00* (2006.01)
*G06T 9/00* (2006.01)
*G06T 7/00* (2017.01)
*G06V 10/25* (2022.01)

(52) U.S. Cl.
CPC ............ *A61B 6/5235* (2013.01); *A61B 6/469* (2013.01); *A61B 6/505* (2013.01); *A61B 6/5205* (2013.01); *A61B 6/5217* (2013.01); *G06T 7/0012* (2013.01); *G06T 9/00* (2013.01); *G06V 10/25* (2022.01); *G06T 2207/10116* (2013.01); *G06T 2207/20081* (2013.01); *G06T 2207/30008* (2013.01)

(58) Field of Classification Search
None
See application file for complete search history.

(56) References Cited

U.S. PATENT DOCUMENTS

| | | | |
|---|---|---|---|
| 7,394,946 B2* | 7/2008 | Dewaele | G06T 7/66 382/128 |
| 10,896,356 B2* | 1/2021 | Dinerstein | G06T 3/0093 |
| 2019/0361439 A1* | 11/2019 | Zeng | G06V 10/82 |
| 2020/0126234 A1* | 4/2020 | Yokota | G06T 7/174 |
| 2020/0349439 A1* | 11/2020 | Luo | G06N 3/0454 |
| 2020/0356842 A1* | 11/2020 | Guo | G06F 17/15 |

* cited by examiner

*Primary Examiner* — Nancy Bitar
(74) *Attorney, Agent, or Firm* — Anova Law Group, PLLC

(57) ABSTRACT

A method for performing computer-aided diagnosis (CAD) based on a medical scan image includes: pre-processing the medical scan image to produce an input image, a flipped image, and a spatial alignment transformation corresponding to the input image and the flipped image; performing Siamese encoding on the input image to produce an encoded input feature map; performing Siamese encoding on the flipped image to produce an encoded flipped feature map; performing a feature alignment using the spatial alignment transformation on the encoded flipped feature map to produce an encoded symmetric feature map; and processing the encoded input feature map and the encoded symmetric feature map to generate a diagnostic result indicating presence and locations of anatomical abnormalities in the medical scan image.

17 Claims, 13 Drawing Sheets

DEVICE AND METHOD FOR COMPUTER-AIDED DIAGNOSIS BASED ON IMAGE

CROSS-REFERENCE TO RELATED APPLICATION

This application claims the priority of U.S. Provisional Patent Application No. 62/958,965, filed on Jan. 9, 2020, the entire contents of which are incorporated herein by reference.

TECHNICAL FIELD

The present disclosure relates to the technical field of computer-aided diagnosis (CAD) and, in particular, to a device and method for computer-aided diagnosis (CAD) based on an image.

BACKGROUND

Medical imaging techniques, such as magnetic resonance imaging (MM), computed topography (CT), X-ray imaging, and ultrasound imaging, are widely used in medical diagnosis and treatment planning. Usually the information obtained by various imaging modalities needs to be analyzed and evaluated by radiologists or other medical professionals to make a diagnosis. There is an emerging need for computer-aided diagnosis (CAD) to assist doctors in the interpretation of medical images, and to improve the efficiency, accuracy and cost effectiveness of the medical imaging evaluation. For example, trauma pelvic X-rays (PXRs) are essential for instantaneous pelvic bone fracture detection. However, small, pathologically critical fractures can be missed, even by experienced clinicians, under the very limited diagnosis times allowed in urgent care. As a result, computer-aided diagnosis (CAD) of fractures has very high demands to save time and assist physicians to detect (otherwise) missed fractures more accurately and reliably.

Several studies have investigated the use of symmetry cues for CAD, with aiming to find abnormalities in application such as neuroimaging, breast cancer detection, and stroke diagnosis. Usually, symmetry cues are defined in the image or shape space for these applications. However, under less constrained scenarios, especially ones using projection-based imaging modalities in an emergency room setting, e.g., PXRs, image asymmetries do not always indicate positive clinical findings, as they are often caused by other non-pathological factors such as patient pose, bowel gas patterns, and clothing. For these settings, a workflow better mirroring the clinical practice, i. e. robust analysis across semantic anatomical symmetries, is needed.

SUMMARY

In one aspect of the present disclosure, a method for performing computer-aided diagnosis (CAD) based on a medical scan image is provided. The method includes: pre-processing the medical scan image to produce an input image, a flipped image, and a spatial alignment transformation corresponding to the input image and the flipped image; performing Siamese encoding on the input image to produce an encoded input feature map; performing Siamese encoding on the flipped image to produce an encoded flipped feature map; performing a feature alignment using the spatial alignment transformation on the encoded flipped feature map to produce an encoded symmetric feature map; and processing the encoded input feature map and the encoded symmetric feature map to generate a diagnostic result indicating presence and locations of anatomical abnormalities in the medical scan image.

In certain embodiments, pre-processing the medical scan image includes: detecting a plurality of landmarks in the medical scan image, the plurality of landmarks including one or more pairs of bilateral symmetric landmarks; identifying an axis of bilateral symmetry from the plurality of landmarks; generating the flipped image as a mirror image of the input image with respect to the axis of bilateral symmetry; and generating the spatial alignment transformation as a matrix that maps the flipped image to the input image to align the plurality of landmarks.

In certain embodiments, pre-processing the medical scan image further includes: extracting region of interests from the input image, the flipped image, and the spatial alignment transformation.

In certain embodiments, processing the encoded input feature map and the encoded symmetric feature map includes: performing fusion on the encoded input feature map and the encoded symmetric feature map to produce an encoded joint feature map; and performing decoding on the encoded joint feature map to produce a detection probability map of the anatomical abnormalities.

In certain embodiments, performing fusion on the encoded input feature map and the encoded symmetric feature map includes performing a concatenation operation on the encoded input feature map and the encoded symmetric feature map.

In certain embodiments, the concatenation operation is performed within a transition module after a rectified linear unit (Relu) operation.

In certain embodiments, processing the encoded input feature map and the encoded symmetric feature map further includes: performing a Siamese feature comparison on the encoded input feature map and the encoded symmetric feature map to produce a feature distance map characterizing abnormality-causing feature asymmetries.

In certain embodiments, performing a Siamese feature comparison includes: performing a dimension reduction on the encoded input feature map and the encoded symmetric feature map; and calculating pixel-wise contrastive loss between the encoded input feature map and the encoded symmetric feature map as L2 distance.

In certain embodiments, performing the dimension reduction includes: projecting the encoded input feature map and the encoded symmetric feature map from a 1024-dimensional space to a 64-dimensional space.

In certain embodiments, the method further includes: receiving a set of training images; pre-processing the training images to produce point-annotated ground-truth images; and performing training of a Siamese neural network based on the training images and the point-annotated ground-truth images.

In certain embodiments, performing training of the Siamese neural network includes: for a point-annotated ground-truth image containing one or more annotation points, transforming each annotation point to a binary regional mask to produce a ground-truth mask; performing multi-scale feature fusion on a corresponding training image using a feature pyramid network to generate a predicted probability map; and calculating a Binary Cross-Entropy loss of predicted probability map against the ground truth mask.

In certain embodiments, the method is implemented by a fully convolutional Siamese network including a plurality of dense blocks, the plurality of dense blocks being split into an encoding portion and a decoding portion at a middle level after a third dense block.

In certain embodiments, the medical scan image is a pelvic X-ray (PXR) image and the diagnostic result includes presence and locations of pelvic fractures in the PXR image.

In another aspect of the present disclosure, a device for performing computer-aided diagnosis (CAD) based on a medical scan image is provided. The device includes a memory storing computer-executable instructions and a processor coupled with the memory. When the computer-executable instructions are executed, the processor is configured to: pre-process the medical scan image to produce an input image, a flipped image, and a spatial alignment transformation corresponding to the input image and the flipped image; perform Siamese encoding on the input image to produce an encoded input feature map; perform Siamese encoding on the flipped image to produce an encoded flipped feature map; perform a feature alignment using the spatial alignment transformation on the encoded flipped feature map to produce an encoded symmetric feature map; and process the encoded input feature map and the encoded symmetric feature map to generate a diagnostic result indicating presence and locations of anatomical abnormalities in the medical scan image.

In certain embodiments, the processor is further configured to: perform fusion on the encoded input feature map and the encoded symmetric feature map to produce an encoded joint feature map; and perform Siamese decoding on the encoded joint feature map to produce a detection probability map of the anatomical abnormalities.

In certain embodiments, the processor is further configured to: perform a Siamese feature comparison on the encoded input feature map and the encoded symmetric feature map to produce a feature distance map characterizing abnormality-causing feature asymmetries.

In certain embodiments, the processor is further configured to: combine the detection probability map and the feature distance map to generate diagnostic result.

In another aspect of the present disclosure, a non-transitory computer-readable storage medium is provided. The non-transitory computer-readable storage medium stores a plurality of instructions. When the plurality of instructions are executed by a processor, they cause the processor to: pre-process a pelvic X-ray (PXR) image to produce an input image, a flipped image, and a spatial alignment transformation corresponding to the input image and the flipped image; perform Siamese encoding on the input image to produce an encoded input feature map; perform Siamese encoding on the flipped image to produce an encoded flipped feature map; perform a feature alignment using the spatial alignment transformation on the encoded flipped feature map to produce an encoded symmetric feature map; and process the encoded input feature map and the encoded symmetric feature map to generate a diagnostic result indicating presence and locations of pelvic fractures in PXR image.

According to certain embodiments, the plurality of instructions further cause the processor to: perform fusion on the encoded input feature map and the encoded symmetric feature map to produce an encoded joint feature map; and perform Siamese decoding on the encoded joint feature map to produce a detection probability map of the pelvic fractures.

According to certain embodiments, the plurality of instructions further cause the processor to: perform a Siamese feature comparison on the encoded input feature map and the encoded symmetric feature map to produce a feature distance map characterizing abnormality-causing feature asymmetries.

BRIEF DESCRIPTION OF THE DRAWINGS

In order to more clearly illustrate the technical solutions in the embodiments of the present disclosure, the drawings used in the description of the embodiments will be briefly described below. It is obvious that the drawings in the following description are only some embodiments of the present disclosure. Other drawings may be obtained by those of ordinary skill in the art based on these drawings.

DETAILED DESCRIPTION

The technical solutions according to the embodiments of the present disclosure described in the following with reference to the accompanying drawings. The described embodiments are only part of the embodiments of the present disclosure, but not all the embodiments. All other embodiments obtained by a person of ordinary skill in the art based on the embodiments of the present disclosure without creative efforts are within the scope of the present disclosure.

The present disclosure provides a device and method for computer-aided diagnosis (CAD) based on medical scan images. In particular, the CAD device and method provided by the present disclosure may be applied in detecting anatomical abnormalities in complex imaging scenarios. For example, the disclosed device and method may be applied to detection of pelvic fraction in emergency-room pelvic X-rays (PXRs). Pelvic fractures are among the most dangerous and lethal traumas, due to their high association with massive internal bleeding. Non-displaced fractures, i.e., fractures that cause no displacement of the bone structures, can be extraordinarily difficult to detect, even for experienced clinicians. The combination of difficult detection coupled with extreme and highly consequential demands on performance motivates improved detection performance and efficiency.

The CAD device may be configured to receive a medical scan image containing anatomical structures, such as a PXR image. The medical scan image may be generated by an imaging device. For example, the medical scan image may be obtained from an X-ray machine, loaded from a memory module, or otherwise provided to the device. The device is configured to perform a neural network processing to identify and locate one or more anatomical abnormalities, such as fractures, from the medical scan image. The neural network may be configured to receive the medical scan image and generate an output to provide diagnostic information. Parameters of the neural network may be generated by a training process configured to receive a training data set containing a plurality of annotated medical images.

Figure 1:
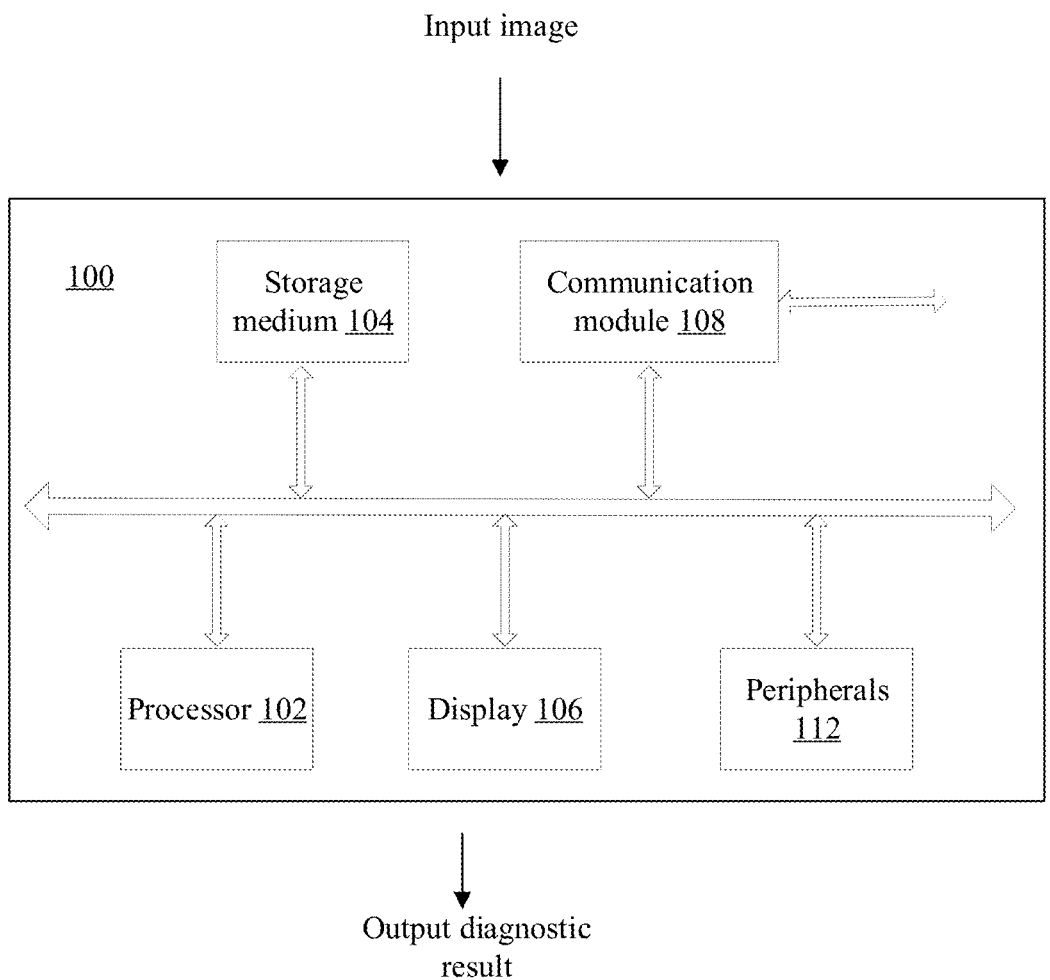
FIG. 1 illustrates a configuration of a computer-aided diagnosis (CAD) device for detecting and locating anatomical abnormalities from a scan image using a neural network according to some embodiments of the present disclosure.

FIG. 1 illustrates a device configuration according to certain embodiments. As shown in FIG. 1, a medical scan image, such as a pelvic X-ray (PXR) image, may be inputted into the CAD device 100 for processing. A detection result may be outputted by the CAD device. In certain embodiments, the detection result may include a probability map showing presence and location of one or more anatomical abnormalities. In certain embodiments, the CAD device 100 may be a computing device including a processor 102 and a storage medium 104. According to certain embodiments, the CAD device 100 may further include a display 106, a communication module 108, and additional peripheral devices 112. Certain devices may be omitted and other devices may be included.

Processor 102 may include any appropriate processor(s). In certain embodiments, processor 102 may include multiple cores for multi-thread or parallel processing. Processor 102 may execute sequences of computer program instructions to perform various processes, such as a neural network processing program. Storage medium 104 may be a non-transitory computer-readable storage medium, and may include memory modules, such as ROM, RAM, flash memory modules, and erasable and rewritable memory, and mass storages, such as CD-ROM, U-disk, and hard disk, etc. Storage medium 104 may store computer programs for implementing various processes, when executed by processor 102. The communication module 108 may include network devices for establishing connections through a network. Display 106 may include any appropriate type of computer display device or electronic device display (e.g., CRT or LCD based devices, touch screens). Peripherals 112 may include additional I/O devices, such as a keyboard, a mouse, and so on. The processor 102 may be configured to execute instructions stored on the storage medium 104 and perform various operations related to a CAD method as detailed in the following descriptions.

Figure 2:
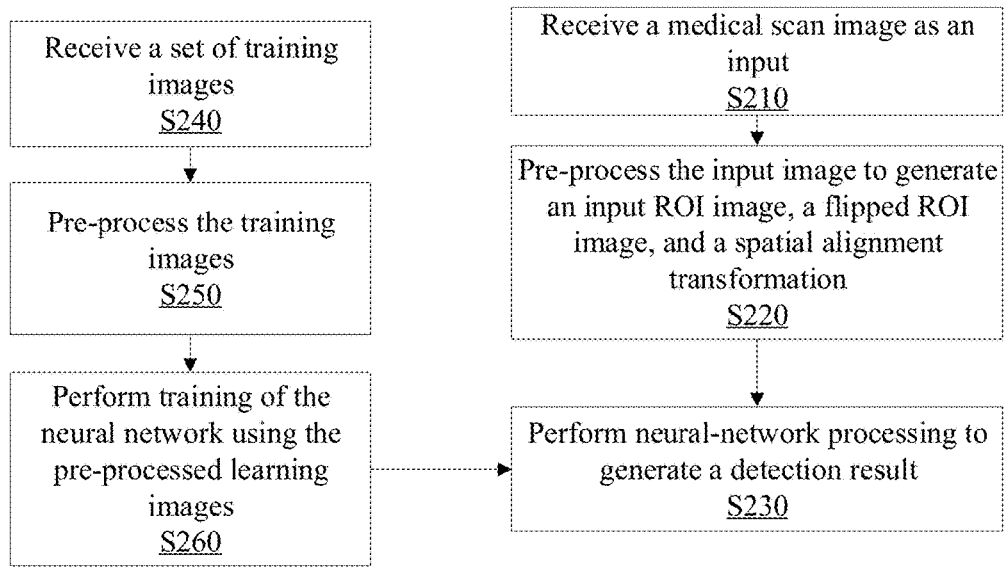
FIG. 2 illustrates a CAD method for detecting and locating anatomical abnormalities from a scan image using a neural network according to some embodiments of the present disclosure.

FIG. 2 illustrates a CAD method 200 for detecting and locating anatomical abnormalities from a scan image using a neural network according to certain embodiments. The method 200 may include the following exemplary steps.

Step S210 is to receive a medical scan image as an input image I. In certain embodiments, the CAD method 200 may be used to process one or more medical scan images, such as one or more X-rays scans, CT scans, PET scans, SPECT scans, MRIs, etc. In certain embodiments, the method may be used to process a pelvic X-ray (PXR) image to detect one or more pelvic factures. The PXR may be generated by an X-ray machine, loaded from a memory module, or otherwise provided as an input to the CAD method.

Step S220 is to pre-process the input image I to generate an input region of interest (ROI) image I', a flipped ROI image $I_f'$, and a ROI spatial alignment transformation T'. Prior to performing image analysis, a few pre-processing steps are applied to the input image. The pre-processing steps may generate an input ROI image I' and a flipped ROI image $I_f'$ according to the input image. A ROI spatial alignment transformation T' may also be generated to spatially align the flipped ROI image $I_f'$ with the input ROI image I'.

Step S230 to perform neural-network processing on the input ROI image I' and the flipped ROI image $I_f'$ to generate a detection result. In certain embodiments, the detection result may include a detection probability map, which is a 2-D map of a spatial distribution of probabilities of abnormalities in the input image. A pixel in the detection probability map having a higher value corresponds to a higher probability of abnormality at the location of the pixel. In certain embodiments, the input image I is a PXR image, and the detection probability map corresponds to a spatial distribution of probabilities of fracture corresponding to an ROI of the PXR image. The detection probability map provides identification and localization of possible fractures in the PXR image. In certain embodiments, the detection result may include a feature distance map, which is a 2-D map charactering abnormality-causing feature asymmetries.

In certain embodiments, a convolutional neural network (CNN) may be used in the neural-network processing. In certain embodiments, a Siamese neural network may be used, where the same weights are used in tandem on the input ROI image I' and the flipped ROI image $I_f'$. Specifically, the Siamese neural network may be an anatomy-aware Siamese network (AASN). The AASN may utilize symmetry in certain anatomical structures to improve detection of abnormalities. For example, the AASN may utilize symmetry in skeletal structures to detect fractures, such as in detection of pelvic fractures from PXR images. In certain embodiments, the AASN performs alignment on feature maps after encoding.

In certain embodiments, the AASN processing may include a Siamese feature fusion process that generates the detection probability map. In certain embodiments, the AASN processing may further include a Siamese feature comparison process for learning embeddings that are sensitive to pathology-related asymmetries and invariant to non-pathology related ones. This may further mitigate an impact of distracting asymmetries that may mislead the model. With a sensible embedding in place, corresponding anatomical regions may be jointly decoded for abnormality detection, allowing the decoder to reliably discover abnormality-causing discrepancies.

In certain embodiments, fully convolutional Siamese networks may be employed as the backbone of the AASN. While previous symmetry modeling methods rely on image-based spatial alignment before encoding, certain embodiments of the present disclosure may perform alignment on the feature maps after encoding. This is motivated by the observation that image asymmetry in PXRs may be caused by many factors, including imaging angle and patient pose. Thus, directly aligning images may be prone to introducing artifacts, which can alter pathological image patterns and make them harder to detect. Certain embodiments of the method provided in the present disclosure may further use a Siamese feature comparison for learning embeddings that are sensitive to pathology-related asymmetries and invariant to non-pathology related ones. This may mitigate the impact of distracting asymmetries that may mislead the model. With a sensible embedding in place, corresponding anatomical regions may be jointly decoded for fracture detection, allowing the decoder to reliably discover fracture-causing discrepancies.

Certain embodiments of the CAD method also include training of the neural network. The CAD method according to these embodiments also includes the additional steps. Step 240 is to receive a set of training images. The training images may be of a same type of medial scan images, such as the as the PXRs.

Figure 3:
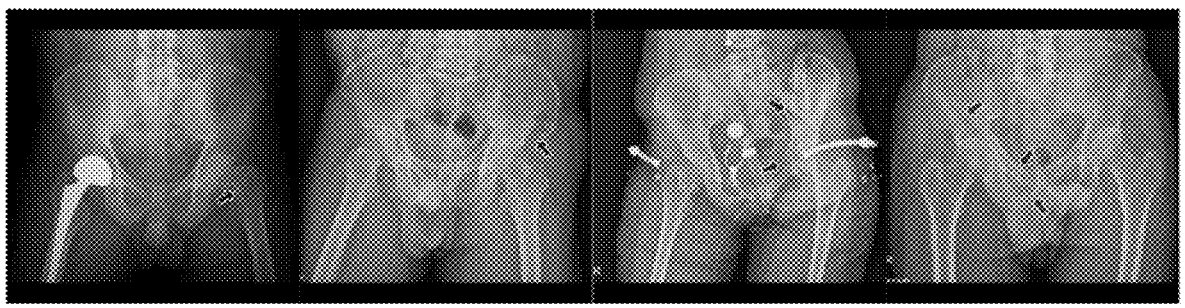
FIG. 3 illustrates examples of point annotations on pelvic X-ray (PXR) images.

Step 250 is to pre-process the training images. The pre-processing of the training image may include annotation pre-processing, where presence and locations of abnormalities in the training images are annotated. According to certain embodiments, the training images are PXRs used to train an AASN to detect pelvic fractures. Unlike typical detection setups, fractures may not be accurately represented by bounding boxes because the definition of a fracture's extent is highly ambiguous. For instance, a fracture may be comminuted, bone breaking into multiple pieces, which can be regarded as one object or multiple objects. It also may not be represented by segmentation, since the boundary of a fracture is also ambiguous. According to certain embodiments, in annotation pre-processing, the method treats the center of each fracture site as annotation, allowing ambiguous fracture conditions to be flexibly represented as one point or multiple points. That is, center points of each fracture site are used to generate point annotations. FIG. 3 illustrates examples of point annotations on PXR images where the point annotations are marked by arrows.

Step 260 is to perform training of the neural network using the pre-processed training images. In certain embodiments, the model may be trained using two losses. The first loss is the pixel-wise binary cross entropy (BCE) between the predicted detection probability map Y and the ground truth M, denoted as $L_b$. The second loss is the pixel-wise contrastive loss between the two feature maps, F and $F_f^!$, denoted as $L_c$. The total loss can be written as $$L = L_b + \lambda L_c, \quad (1)$$

where $\lambda$ is a weight balancing the two losses.

In certain embodiments, a point-guided learning approach is used to perform training of the neural network. Further details of this step will be presented in later description of this disclosure.

Figure 4:
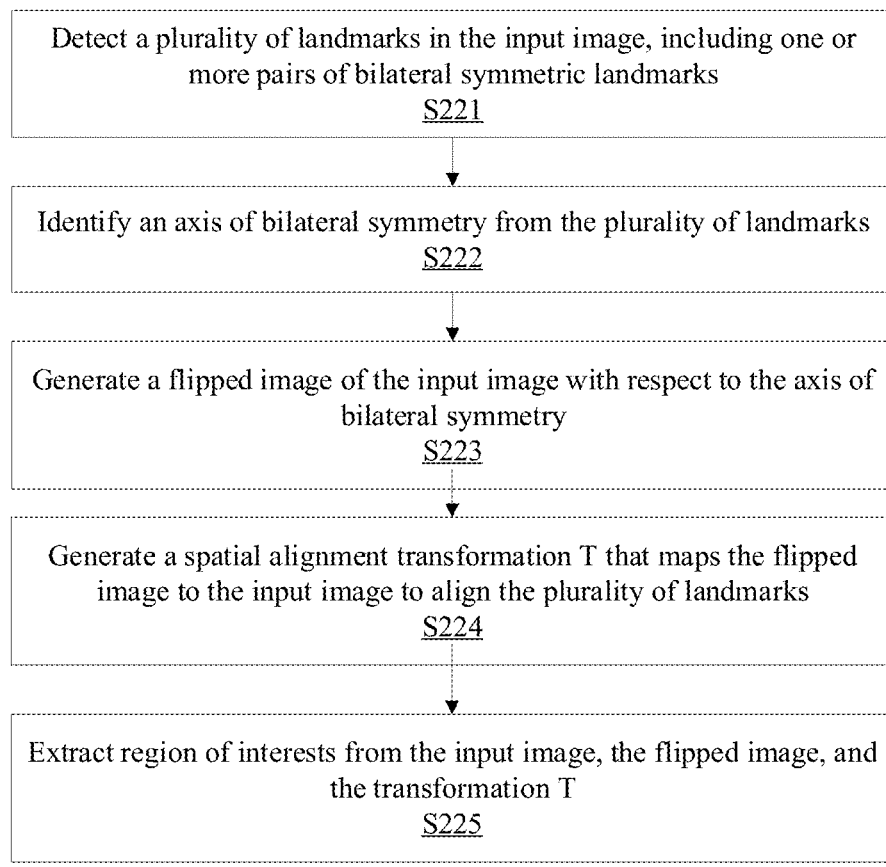
FIG. 4 illustrates an exemplary pre-processing procedure of an input scan image according to some embodiments of the present disclosure.

FIG. 4 illustrates steps of the pre-processing S220 of the input medical scan according to certain embodiments. The workflow may include the following steps as shown in FIG. 3.

Figure 5A:
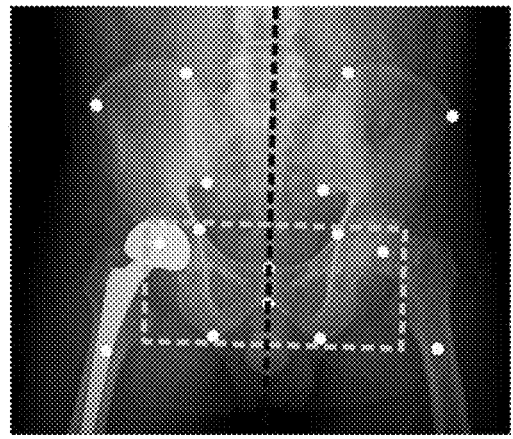
FIG. 5A illustrates an example of skeletal landmarks detected in a PXR image.

Step S221 is to detect a plurality of landmarks in the input image i, including one or more pairs of bilateral symmetric landmarks. In certain embodiments, the input image is a PXR image, and the plurality of landmarks are skeletal landmarks that mark the locations of distinct skeletal features. Since human bodies exhibit bilateral symmetry in anatomical structures including the skeletal structure, pairs of bilateral symmetric landmarks may be identified from the input image. In certain embodiments, graph convolutional network (GCN)-based landmark detection may be used to detect the plurality of landmarks. The landmarks including bilateral symmetric landmarks may be used to exploit symmetry cues by anatomically re-parameterizing the image. If the input image is a PXR image, the landmarks may be used to create an anatomically-grounded warp from one side of the pelvis to the other. FIG. 5A illustrates an example of skeletal landmarks detected in a PXR image. As shown in FIG. 5A, on a PXR image, as shown by the gray-scale image, 16 skeletal landmarks are detected, as shown by the 16 bright dots. The 16 skeletal landmarks include 7 pairs of bilateral symmetric landmarks and 2 non-bilateral landmarks located along a central vertical line. The plurality of landmarks may mark the locations of distinct skeletal features shown on the PXR image. In certain other examples, other quantities of landmarks may be detected in the input image. The present disclosure does not limit the number of the landmarks detected from the input image.

Referring back to FIG. 4, Step S222 is to identify an axis of bilateral symmetry according to the plurality of landmarks. Since the plurality of landmarks detected from the input image include one or more pairs of bilateral symmetric landmarks, an axis of bilateral symmetry may be identified based on the plurality of landmarks. In certain embodiments, the plurality of landmarks detected from the input image include multiple pairs of bilateral symmetric landmarks, and the axis of bilateral symmetry may be identified using a regression algorithm. For example, the axis of bilateral symmetry may be identified by regressing mid-points of landmark pairs as well as the two landmarks at pubic symphysis in a PXR image. The axis of bilateral symmetry may coincide with a central line of anatomical structures shown in the input image. In the example shown in FIG. 5A, the dashed vertical line illustrates the axis of bilateral symmetry identified for the PXR image based on the 16 skeletal landmarks. The axis of bilateral symmetry shown in FIG. 5A may coincide with a central line of the pelvic skeletal structure shown in the PXR image.

Figure 5B:
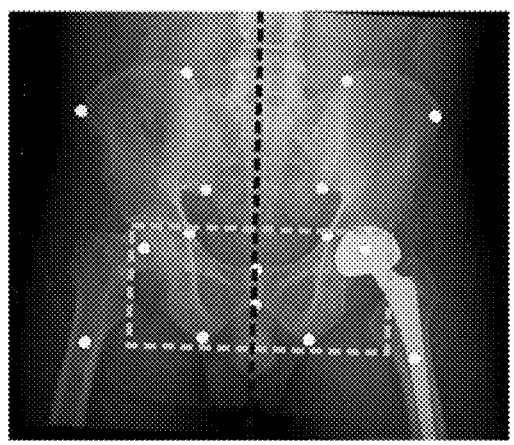
FIG. 5B shows a flipped image of the PXR image in FIG. 5A.

Referring back to FIG. 4, Step S223 is to generate a flipped image $I_f$ of the input image I with respect to the axis of bilateral symmetry. Since the axis of bilateral symmetry has been identified, a mirror transformation with respect to the axis of bilateral symmetry may be performed on the input image to generate the flipped image. FIG. 5B shows the flipped image $I_f$ of the PXR image in FIG. 5A. As shown in FIG. 5B, the flipped image is the mirrored image of the PXR image which switches the left and right halves with respect to the axis of bilateral symmetry. The plurality of the landmarks are also flipped in the left-right direction in the flipped image $I_f$.

Figure 5C:
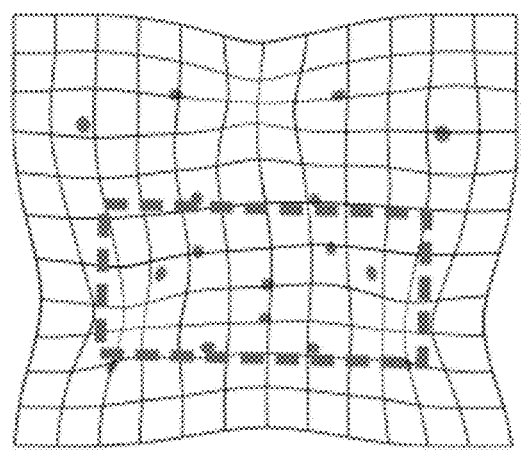
FIG. 5C provides a visualization a spatial alignment transformation that spatially maps the flipped image to the input image shown in FIG. 5A and FIG. 5B.

Referring back to FIG. 4, Step S224 is to generate a spatial alignment transformation T that maps the flipped image $I_f$ to the input image i to align the plurality of landmarks. Due to factures such as imperfect symmetry in the anatomic features, imaging artifact, imaging angle, and patient pose, the plurality of landmarks in the flipped image $I_f$ and the input image i may not be aligned perfectly. A transformation T may be generated to spatially align the pixels in flipped image $I_f$ to the pixels of the input image i. That is, when the transformation T is applied to the flipped image $I_f$, the positions of the landmarks in the flipped image $I_f$ and positions of the landmarks in the input image i may be spatially aligned. The spatial alignment transformation T will be used in the steps in the following desecrations. In certain embodiments, the transformation T may be generated by a thin-plate spline (TPS) warping algorithm given the landmarks that need to be aligned. In certain embodiments, the transformation T is applied on the feature map using bi-linear interpolation to spatially align the features of an encoded flipped image to an encoded input image. FIG. 5C provides a visualization of a deformable transformation hat spatially maps the flipped image $I_f$ to the input image i shown in FIG. 5A and FIG. 5B.

Figure 5D:
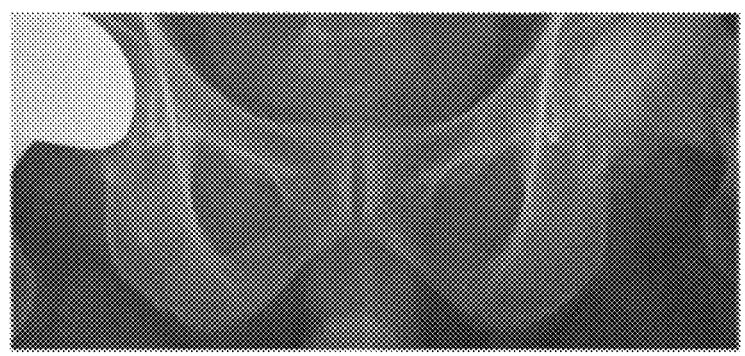
FIG. 5D shows an input region of interest (ROI) image of the PXR image of FIG. 5A.
Figure 5E:
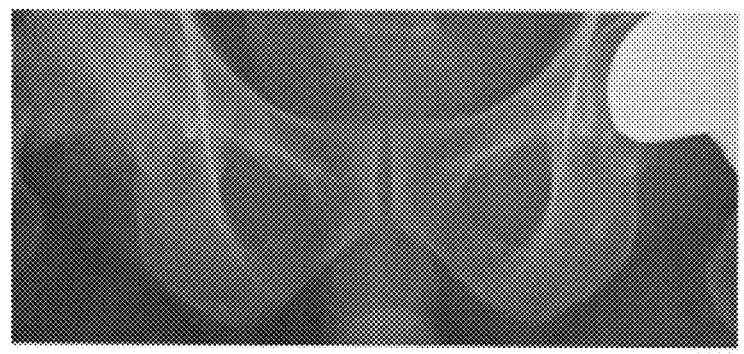
FIG. 5E shows a flipped ROI image of the PXR image of FIG. 5A.
Figure 5F:
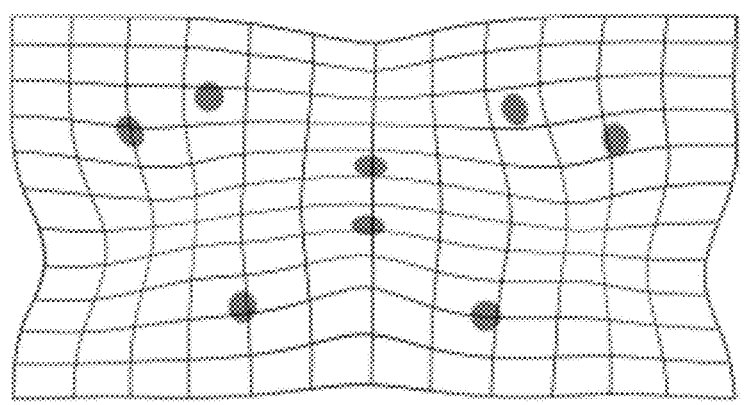
FIG. 5F shows a ROI transformation of the spatial alignment transform of FIG. 5C.

Referring back to FIG. 4, Step S225 is to extract region of interests from the input image, the flipped image, and the transformation T. In certain embodiments, the input image i may exceed a range of a region of interest for diagnostic purposes. In these scenarios, a bounding box may be created to extract region of interests from the input and flipped images and exclude regions that are not of interest for diagnostic purposes. As shown in the examples of FIG. 5A, FIG. 5B, and FIG. 5C, a bounding box may be applied to the input image i, the flipped image $I_f$, and the spatial alignment transformation T. The structures within the bounding box in I and $I_f$ are used for diagnosis in later steps of the CAD method. FIGS. 5D, 5E, and 5F show the input ROI image I', flipped ROI image $I_f'$, and the ROI transformation T' of the input image i, the flipped image and the spatial alignment transformation T, respectively.

Figure 6:
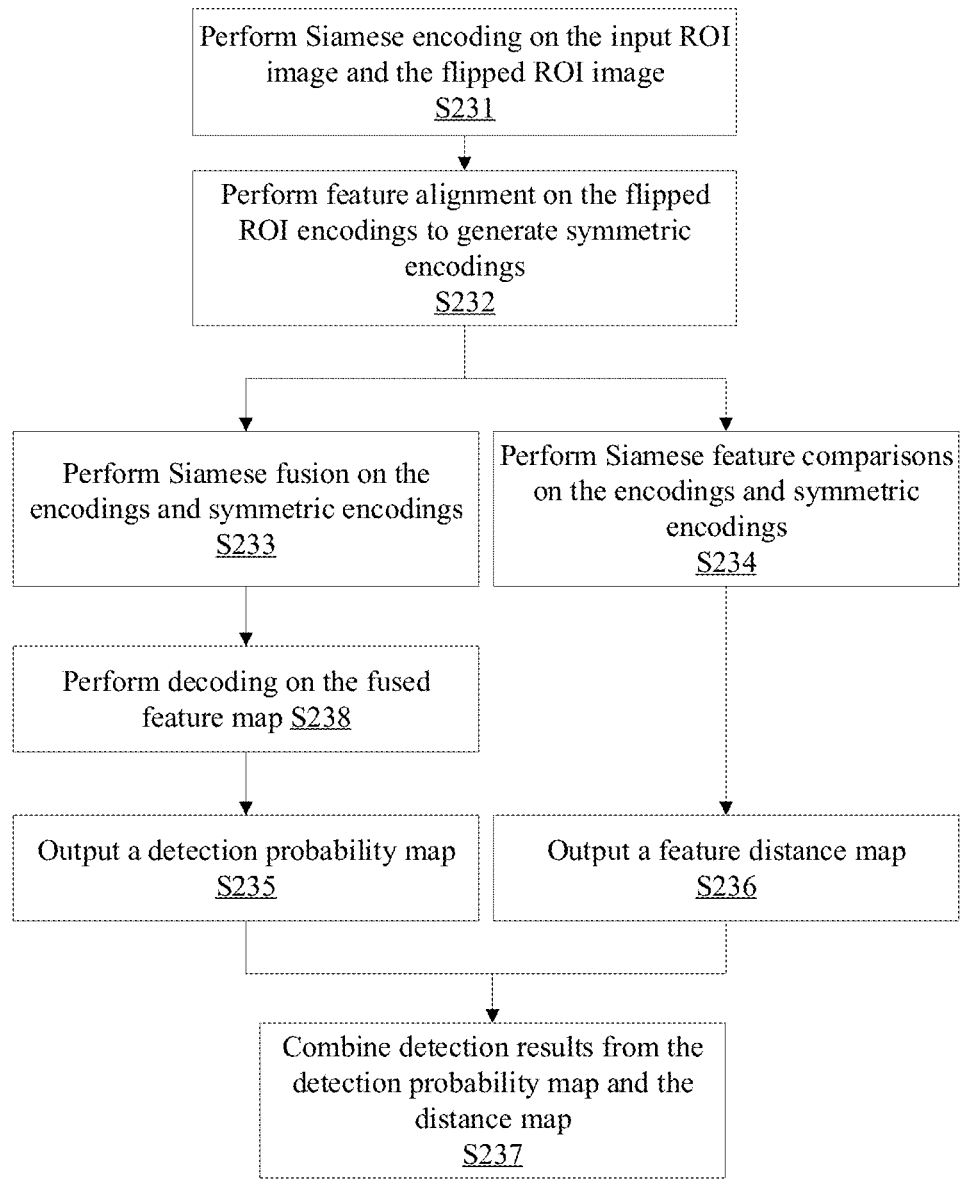
FIG. 6 illustrates an exemplary neural-network processing procedure to generate detection results according to some embodiments of the present disclosure.

FIG. 6 illustrates steps of the neural-network processing S230 to generate detection results according to certain embodiments. The workflow may include the following steps as shown in FIG. 5. FIGS. 6A, 6B, and 6C illustrates more detailed operations of an architecture of AASN according to certain embodiments.

As shown in FIG. 6, Step S231 is to perform Siamese encoding on the input ROI image and the flipped ROI image. Siamese encoding on the input ROI image generates feature encodings of the input ROI image. Siamese encoding on the flipped ROI image generates feature encodings of the flipped ROI image. Step 232 is to perform feature alignment on the flipped ROI encodings to generate symmetric encodings. Operations in Step S231 and Step 232 are further illustrated in FIG. 7A.

Step S233 is to perform Siamese fusion on the encodings and symmetric encodings to form a fused feature map. Step S238 is to perform decoding on the fused feature map to generate a detection probability map, which may be outputted in Step 235. Operations in Step S233, S238, and Step S235 are further illustrated in FIG. 7B.

Step S234 is to perform Siamese feature comparisons on the encodings and symmetric encodings. The Siamese feature comparisons may generate a distance map, which may be outputted in Step 236. Operations in Step S234 and Step S236 are further illustrated in FIG. 7C. In certain embodiments, as shown in Step S237, the outputs from Siamese fusion and Siamese feature comparison may be combined to improve detection performance.

In certain embodiments, the AASN may be implemented with a dense convolutional network (DenseNet). In certain embodiments, the AASN may contain a fully convolutional Siamese network with a DenseNet-121 backbone. In certain other embodiments, the AASN may contain other types of DenseNet backbones. The DenseNet backbone includes a plurality of dense blocks. The plurality of dense blocks may be split into two portions, an encoding portion and a decoding portion. The AASN allows the backbone network to be split flexibly at any block. For example, in certain embodiments, the plurality of dense blocks may be split at a middle level after the third dense block, where the features are deep enough to encode the local anatomical pattern, but has not been pooled too heavily so that the textual information of small fractures are lost.

Figure 7A:
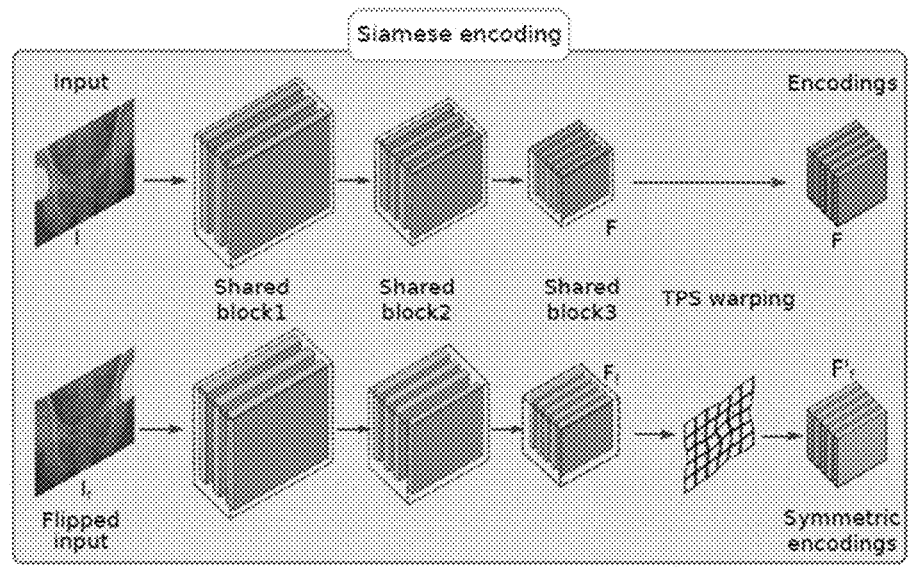
FIG. 7A illustrates a process of Siamese according to some embodiments of the present disclosure.

As shown in FIG. 7A, the encoding layers follow a Siamese structure, with two streams of weight-shared encoding layers taking the two images input ROI image I' and flipped ROI image $I_f'$ as inputs. The encoder outputs F and $F_f$ provide feature representations of the original image and the flipped image, respectively. The spatial alignment transform T is applied on $F_f$, resulting in symmetric encoding $F_f'$, aligning corresponding features in F and $F_f'$. The two aligned feature maps F and $F_f'$ may then be fused and decoded to produce a detection probability map Y. A feature comparison may be also performed based on the two aligned feature maps F and $F_f'$ to produce a distance map Y.

The purpose of encoding the flipped image is to provide a reference of the symmetric counterparts, $F_f$, which may be incorporated with the feature F to facilitate detection of abnormalities. To provide a meaningful reference, $F_f$ needs to be spatially aligned with F, so that features with the same index or coordinates in the two feature maps may encode the same symmetric anatomies of the patient.

In some previous methods, bilateral images have been directly aligned before encoding. However, when large imaging angle and patient pose variations are present, image alignment is prone to introducing artifacts, which can increase the difficulty of abnormality detection. Therefore, instead of directly aligning the flipped image, the method provided by the present application applies the transform T on the feature map $F_f$ to align it with F, resulting in $F_f'$. The aligned feature maps F and $F_f'$ are fused to produce a joint feature map, where every feature vector encodes the visual patterns from symmetrical anatomies. This allows the decoder to directly incorporate symmetry analysis into fracture detection.

Figure 7B:
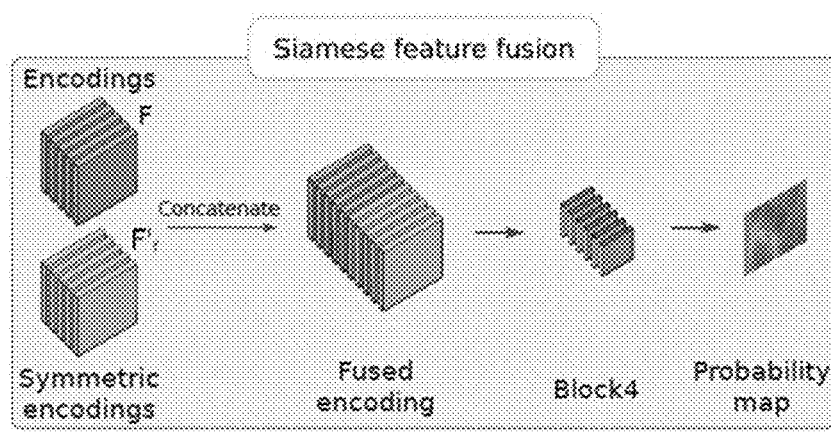
FIG. 7B illustrates a process of Siamese fusion according to some embodiments of the present disclosure.
Figure 8A:
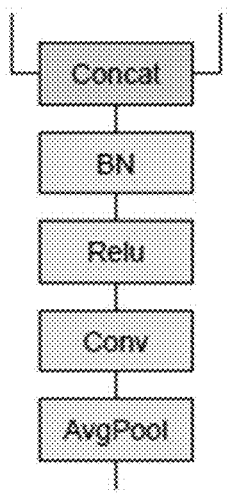
FIG. 8A illustrates an implementation of a transition module according to some embodiments of the present disclosure.
Figure 8B:
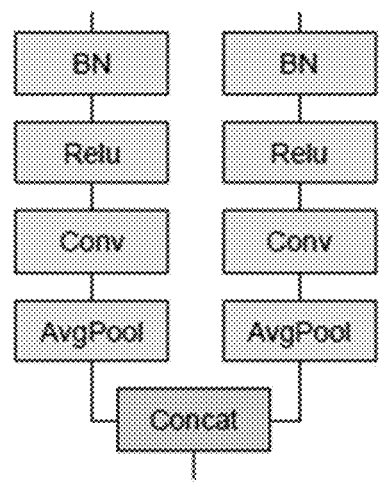
FIG. 8B illustrates an implementation of a transition module according to certain other embodiments of the present disclosure.
Figure 8C:
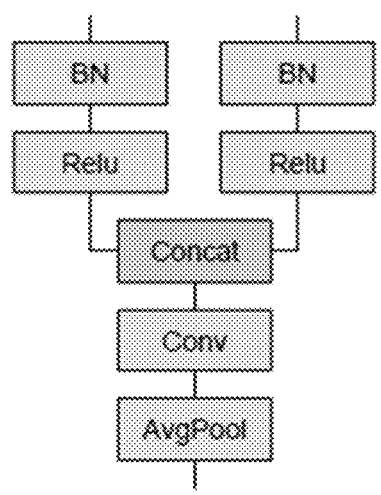
FIG. 8C illustrates an implementation of a transition module according to certain other embodiments of the present disclosure.

As shown in FIG. 7B, in certain embodiments, the feature maps F and $F_f'$ may be fused by concatenation. The concatenation operation involves modification of the transition module between the dense blocks. This may be implemented by a variety of manners. In certain embodiments, the consternation may be performed before the transition module is performed. In certain other embodiments, the consternation may be performed after the transition module is performed. In certain other embodiments, the consternation may be performed within the transition module. FIGS. 8A, 8B, and 8C illustrate examples of implementation of the transition module. As shown in FIGS. 8A-8C, the transition module in DenseNet may include sequential operations of batch normalization (BatchNorm or BN), rectified linear unit (Relu), convolution (Cony) and average pooling (AvgPool). The concatenation operation may be performed before the BN layer (shown in FIG. 8A) or after the AvgPool layer (as shown in FIG. 8B). In certain embodiments, as shown in FIG. 8C, the concatenation operation may be performed inside the transition module after the Relu layer. The arrangement shown in FIG. 8C may cause minimal structural changes to the DenseNet model. Specifically, the only layer affected in the DenseNet may be the 1×1 Cony layer after the concatenation, whose input channels are doubled. All other layers remain the same, allowing the leverage of ImageNet pre-trained weights.

After the fusion operation is completed, a probability map may be generated as abnormality detection result to alert the clinician of the presence of an anatomical abnormality, such as a fracture, present in the input image and also to guide his or her attention to the locations of high probability of presence of anatomical abnormality. In the scenario of pelvic fracture diagnosis using PXRs, since pelvis fractures can be very difficult to detect, even when there is a known fracture, this localization is a key feature over-and-above image-level predictions.

Figure 7C:
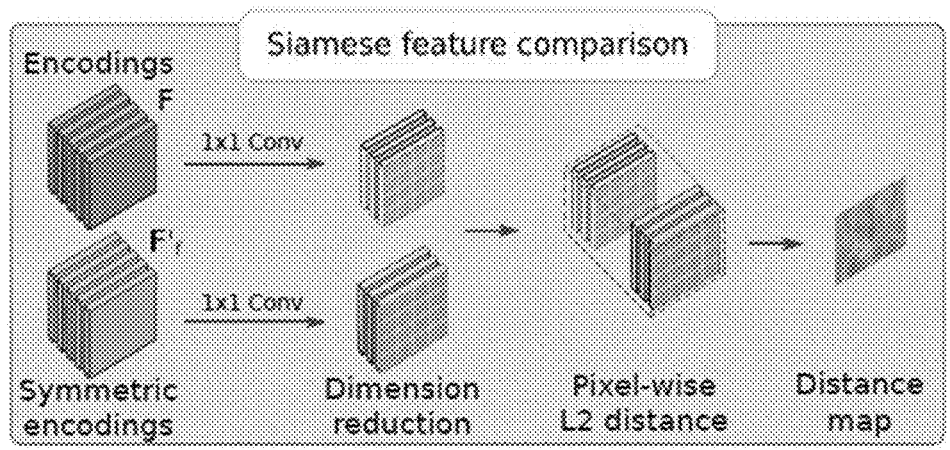
FIG. 7C illustrates a process of Siamese comparison according to some embodiments of the present disclosure.

In certain embodiments, additional advancements may be made in the symmetric analysis by using Siamese feature comparison. A process of the Siamese feature comparison is shown in FIG. 7C. In certain scenarios, image asymmetry may be caused by pathological abnormalities, such as a fracture, or spurious non-pathological factors, such as soft tissue shadows, bowel gas patterns, clothing and foreign bodies. These factors may be visually confusing, causing false positives. During implementation of the AASN, feature map F may be trained to be insensitive to the non-pathological factors and thus less prone to false positives by minimizing the pixel-wise distance between F and $F_f'$ in areas without fracture. On the other hand, in areas affected by fractures, image asymmetry would naturally occur.

In certain embodiments, the above idea may be implemented using pixel-wise contrastive loss between F and $F_f'$, as shown in Equation 2:

$$L_c = \sum_x \begin{cases} d(F(x), F_f'(x))^2 & \text{if } x \notin \hat{M} \\ \max(0, m - d(F(x), F_f'(x)))^2 & \text{if } x \in \hat{M} \end{cases} \quad (2)$$

where x denotes the pixel coordinate, d denotes a distance metric, M denotes the mask indicating areas affected by fractures, and m is a margin governing the dissimilar of fracture-causing feature asymmetries. The mask M needs to consider abnormalities in both sides of the input image as they all can cause abnormality-causing asymmetries. It may be calculated as Equation 3:

$$\hat{M} = M \cup T \cdot M_f \quad (3)$$

where $T \cdot M_f$ is M flipped with respect to the symmetry axis and TPS is applied.

In certain embodiments, the features F(x) and $F_f'(x)$ may be high dimensional (for example, having a dimension of 1024), a dimensionality reduction may be performed as a part of the distance metric. For example, they may be projected to a 64-dimensional space by a learnable projection parameterized by W. The distance metric may then be defined as the L2 distance of the projected vectors, written as:

$$d(F(x), F_f'(x)) = \|WF(x), WF_f'(x)\|_2, \quad (4)$$

where $W \in \mathbb{R}^{64 \times 1024}$ denotes the learnable weights of the projection and remains the same for every coordinate x.

The Siamese feature comparison may produce a feature distance map that quantifies abnormality-related asymmetry in the input image. In certain embodiments, the detection probability map and the feature distance map may be combined to generate diagnostic output.

Figure 9:
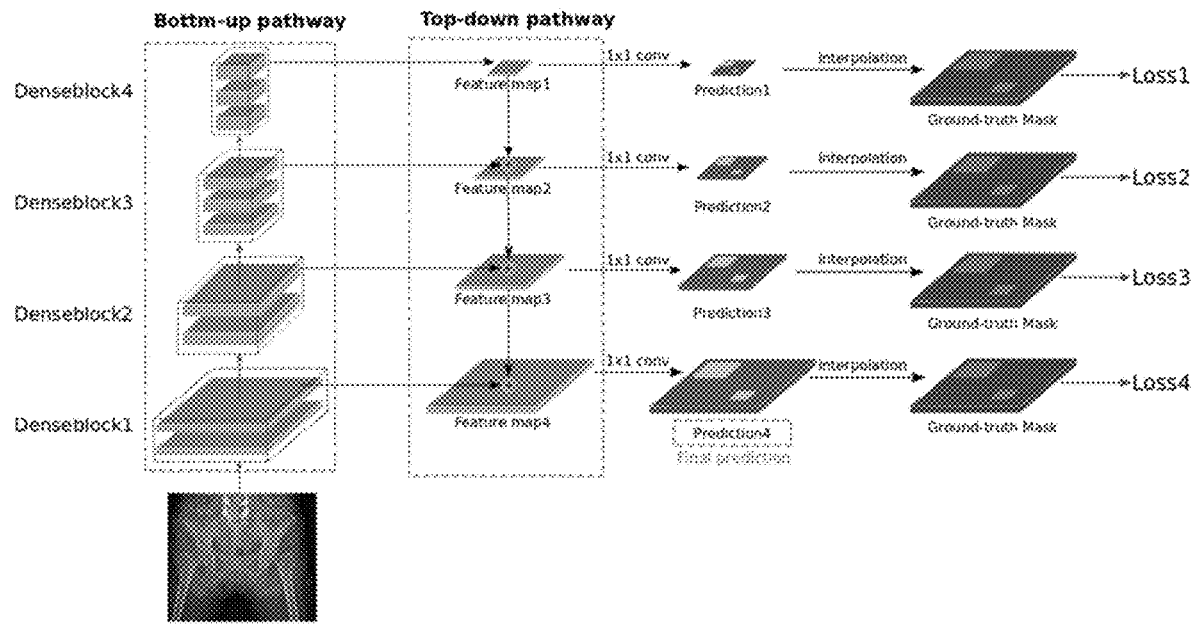
FIG. 9 illustrates a workflow of a neural network training process according to some embodiments of the present disclosure.

FIG. 9 illustrates a workflow of neural network training process S260. In certain embodiments, the training process is a point-guided learning process for universal pelvis fracture detection from PXRs.

To effectively use the ground-truth (GT) point supervision, the method may transform each fracture point in a PXR image to a binary regional mask and formulate the bone fracture detection as a dense prediction task, instead of the image-level binary classification. Given a fracture PXR image i with size $S_I$, and a set of feature maps F={$F_1$, $F_2$, $F_3$, $F_4$} with different size $S_F$={$S_{F1}$, $S_{F2}$, $S_{F3}$, $S_{F4}$} (as shown in FIG. 9 in Top-down pathway), the method may set the GT fracture mask the same size as the highest resolution feature layer, i.e. $S_{F4}$. Let the ratio between the image size and the feature map size $S_{F4}$ be denoted as $$r = \frac{s_F}{s_I}.$$

Given a fracture point coordinate ($x_0$, $y_0$) in an image, the corresponding point coordinate in a GT mask is:

$$p_{annotation} = (\lfloor r \times x_0 \rfloor, \lfloor r \times y_0 \rfloor) \quad (5)$$

Once $p_{annotation}$ is calculated, the method may use it as the center to generate the GT fracture mask by calculating the Chebyshev distance between each grid coordinate and the fracture point coordinate in the GT mask M as follow:

$$M_{ij} = \begin{cases} 1, \text{ if } D_{Chebyshev}(p_{ij}, p_{annotation}) < s \\ 0, \text{ else} \end{cases} \quad (6)$$

where $p_{ij} \in M$, $M_{ij}$ denotes the mask value at position (i, j) and s is the potential fracture size tuned experimentally. For the feature maps with different sizes than $S_{F4}$, the method may resample them to be the same size as $S_{F4}$.

In addition, for images without facture findings, the method may simply generate a GT mask with all values set to be zero:

$$M_{ij} = 0 \text{ for } (i,j) \in M_i \quad (7)$$

As shown in FIG. 9, the network may be constructed with two parallel inversive pathways, named the bottom-up pathway and the top-down pathway. The bottom-up pathway takes an PXR image as input and compute the hierarchical feature channels at different scales. Depending on the size of the feature map, this process can be divided into several stages. While the low-level features have finer resolution, providing more localized activations, the feature maps generated from the higher levels encode more global semantic information. As such, the top-down pathway aims to integrate the feature maps from high to low levels, producing a multi-scale feature representation in which all levels encode rich semantic information. The method may copy the last convolutional layers in each stage to the top-down pathway, which are denoted as {$C_1$, $C_2$, $C_3$, $C_4$}. The high-level feature maps in the top-down pathway have larger channel dimensions but smaller spatial size.

Figure 10:
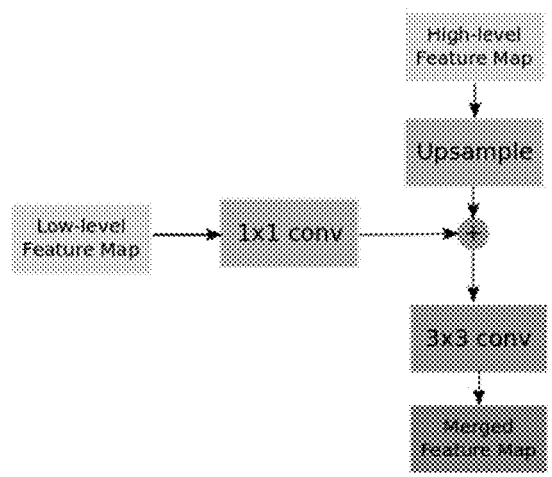
FIG. 10 illustrates a feature fusion process in feature pyramid network (FPN) according to some embodiments of the present disclosure.

FIG. 10 illustrates a feature fusion process in feature pyramid network (FPN). As shown in FIG. 10, to integrate them with $\{C_1, C_2, C_3, C_4\}$, the method may up-sample the high-level feature maps first, and then, merge the up-sampled feature maps with the corresponding bottom-up maps (which are fed into a 1×1 convolutional layer to generate the same channel numbers) by element-wise addition. We denote the merged final feature maps as $\{F_1, F_2, F_3, F_4\}$. To produce the fracture prediction, each feature map in $\{F_1, F_2, F_3, F_4\}$ is sent into a 1×1 convolution layer to generate the predicted probability map, denoted as $P_1$, $P_2$, $P_3$, $P_4$. The predicted probability maps $P_1$, $P_2$, $P_3$ are upsampled to match the size of $P_4$, which is the same as the GT fracture mask size. All four probability maps may be used during training for calculating loss to provide side supervisions. During inference, the method may use the last prediction $P_4$ as the final output. The feature pyramid structure keeps high-level semantics throughout the network, making the model robust to detect pelvis abnormality across a large range of scales.

With the predicted probability maps $P=\{P_1, P_2, P_3, P_4\}$, Binary Cross-Entropy (BCE) loss may be calculated against the ground-truth mask and is used to train the network:

$$l_i = \sum_n -[\widehat{p_n} \cdot \log p_n + (1 - \widehat{p_n}) \cdot \log(1 - p_n)] \quad (8)$$
$$\mathcal{L} = \sum_i l_i$$

where i is the number of independent predictions from different stages, and n is the number of pixels in the predicted probability map. The method may adopt different strategies to calculate the loss for positive and negative PXR images. For PXR images with fractures, the method may only use the losses computed within the positive regions to train the network. To be specific, when calculating the pixel-wise loss between the predicted probability maps and the ground-truth mask, the method may only consider the loss within each s×s region covered by the fracture annotation. In this setting, the method may ignore the influence of regions outside of the s×s fracture annotation, which is able to handle the fracture size inconsistency, since the accurate bone fracture range at each point annotation location is not accurately known. On the other hand, for PXR images without fractures, the whole is considered as negative. Therefore, for the PXR images with fractures, the GT mask is not only used to compute the loss, but also used to mask out the only fracture positive regions for the loss computation.

Some examples demonstrating the performance of the forgoing method based on AASN according to certain embodiments are presented in the following description. The examples focus on detecting fractures on the anterior pelvis including pubis and ischium, an anatomically symmetric region with high rate of diagnostic errors and life-threatening complications in the clinical practice.

For sample dataset, the AASN is evaluated on a real-world clinical dataset collected from the Picture Archiving and Communication System (PACS) of a hospital's trauma emergency department. The images have a large variation in the imaging conditions, including viewing angle, patient pose and foreign bodies shown in the image. Fracture sites in these images are labeled by experienced clinicians, combining multiple sources of information for confirmation, including clinical records and computed tomography scans. The annotations are provided in the form of points, due to inherent ambiguity in the defining fracture as object. In total, there are 2359 PXRs, and 759 of them have at least one anterior pelvic fracture site. All experiments are conducted with five-fold cross-validation with a 70%/10%/20% training, validation, and testing split, respectively.

Figure 11:
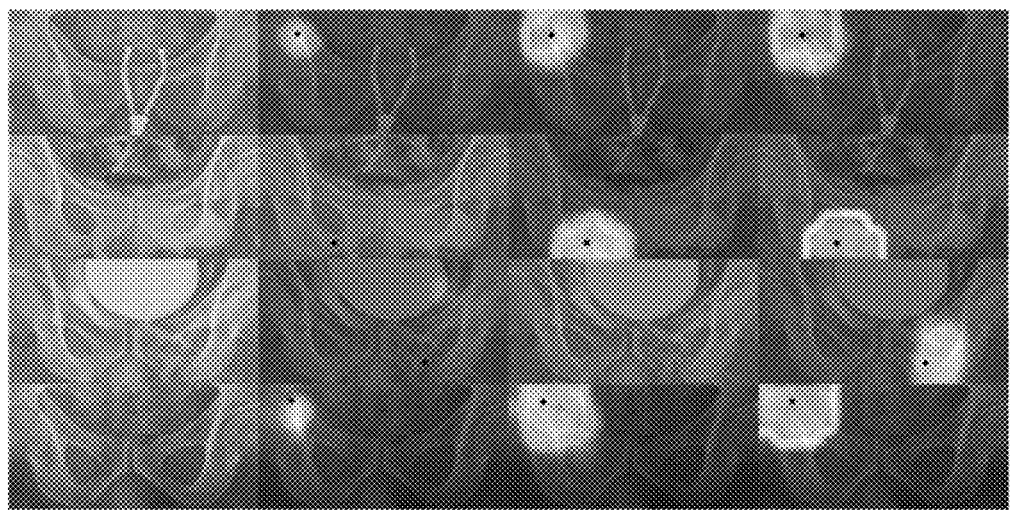
FIG. 11 provides visualization of detection probability maps generated based on five example PXR images.

In the following examples, the AASN is implemented with a DenseNet-121 backbone. The ROIs of the anterior pelvis are extracted and resized to 256×512. The supervision mask for the detection probability prediction branch is produced by dilating the annotation points to circle masks with a radius of 50. The models are implemented using PyTorch, an open source machine learning library, and initialized with ImageNet pre-trained weights. All models are optimized by an algorithm for first-order gradient-based optimization of stochastic objective functions (Adam) with a learning rate of $10^{-5}$. For the pixel-wise contrastive loss, a hyperparameter setting m=0.5 as the margin, and $\lambda$=0.5 to balance the total loss are used. FIG. 11 provides visualization of the detection probability maps generated based on five example PXR images. The left panel shows the pubis ROIs in the PXRs, and the right panels shows the corresponding detection probability maps calculated with the AASN. For performance comparison, detection probability maps are also calculated using a vanilla DenseNet-121 without considering symmetry. The results of the vanilla DenseNet-121 are shown in the middle panel of FIG. 11. Non-displaced fractures that do not cause bone structures to be large disrupted are visually ambiguous and often missed by the vanilla DenseNet-121 without considering symmetry. Comparison between the fracture site and its symmetric bone reveals that the suspicious pattern only occurs on one side and is likely to be fracture. This intuition is in line with the results, by incorporating symmetric features, some of the ambiguous fractures can be detected. By employing the feature comparison module, AASN is able to detect more fracture, hypothetically owing to the better feature characteristics learned via feature comparison.

For evaluation metrics, the model's performance is first assessed as an image-level classifier, which is a widely adopted evaluation approach for CAD devices. The image-level abnormality reporting is of utmost importance in clinical work-flow because it directly affects the clinical decision. The maximum value of the output detection probability map is taken as the classification output. A receiver operating characteristic curve (ROC) is generated based on the maximum value. An area under the ROC Curve (AUC) and an Average Precision (AP) are used to evaluate the classification performance. The Youden's index, as well as the recall (Youden's R) and specificity (Youden's S) are also calculated associated with the AUC.

TABLE 1

| Fracture detection performance of the AASN | | | | |
| --- | --- | --- | --- | --- |
| AUC | AP | Youden's Index | Youden's R | Youden's S |
| 97.71% | 96.36% | 88.37% | 92.87% | 95.50% |

Figure 12A:
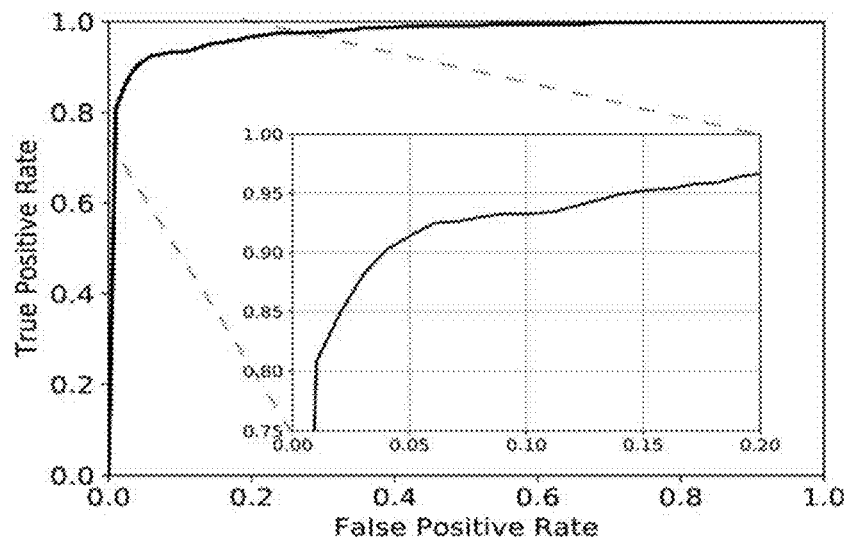
FIG. 12A shows a receiver operating characteristic (ROC) curve illustrating performance of a CAD method according to certain embodiments.
Figure 12B:
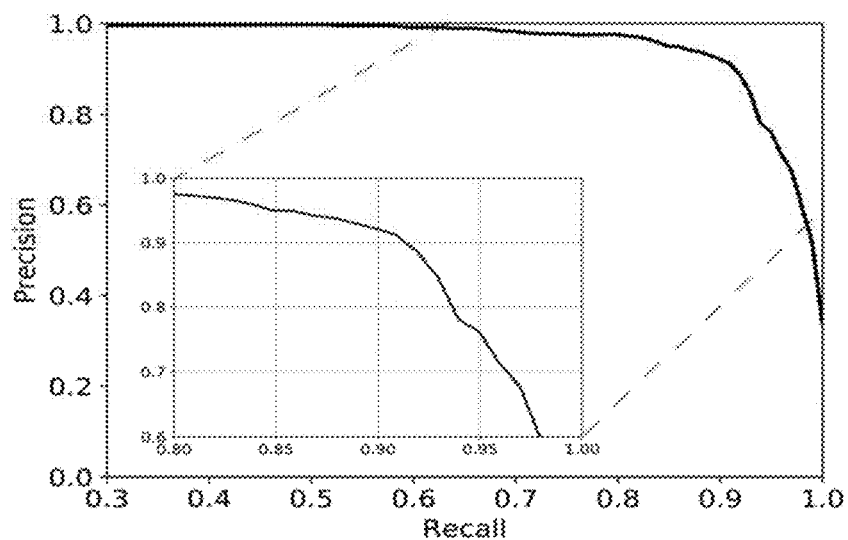
FIG. 12B shows a Precision-Recall (PR) curve corresponding to the ROC curve of FIG. 12A.

The ROC and the Precision-Recall (PR) curves are shown in FIG. 12A and FIG. 12B, respectively. Evaluation metrics of fracture detection performance are summarized in Table 1, including AUC, AP, Youden's index, Youden's R, and Youden's S of the detection performance. AASN provides an AP score of 96.36% for the sample dataset of 2359 PXRs.

The high AP score (above 95%) is significant. For instance, false positives are reduced by 20% if the recall increase from 95% to 96%.

Ablation studies of the AASN have also been conducted to analyze the contributions of its multiple features, including 1) Siamese feature fusion (referred to as FF); 2) feature warping and alignment (referred to as FA) and 3) Feature comparison learning using contrastive loss (referred to as FC). Five methods have been used for comparison including: 1) Vanilla DenseNet-121 (referred to as vanilla) without any AASN modules; 2) FF which includes Siamese feature fusion; 3) FF-FA which includes feature warping and alignment on top of FF; 4) FF-FC which includes feature comparison module on top of FF; and 5) FF-FA-FC which includes AASN with all three modules. Table 2 summarizes the classification performances of these methods.

TABLE 2

Ablation study of AASN. Vanilla DenseNet121 is trained without the Siamese network.

| Method | AUC | AP | Youden's Index | Youden's R | Youden's S |
|---|---|---|---|---|---|
| Vanilla | 96.52% | 94.16% | 84.00% | 90.49% | 93.50% |
| FF | 96.93% | 94.35% | 85.36% | 90.11% | 95.25% |
| FF-FA | 97.20% | 94.97% | 87.41% | 92.22% | 95.19% |
| FF-FC | 97.46% | 95.32% | 86.78% | 90.10% | 96.68% |
| FF-FA-FC | 97.71% | 96.36% | 88.37% | 92.87% | 95.50% |

The effect of Siamese feature fusion is reflected in the comparisons: Vanilla vs. FF and Vanilla vs. FF-FA. Both FF and FF-FA are able to out-perform Vanilla, although by a different margin due to the different alignment methods used. In particular, compared to Vanilla, the Youden's indexes are improved by 1.36% and 3.41% using FF and FF-FA, respectively. These improvements are hypothetically owing to the incorporation of the visual patterns from symmetric body parts, which provide reference for differentiating visually ambiguous fractures.

The effect of feature warping and alignment is reflected in the comparisons of: FF vs. FF-FA and FF-FC vs. FF-FA-FC. The ablation study shows that, by using the feature warping and alignment, the performances of both FF and FF-FC are both significantly improved. In particular, the Youden's indexes are improved by 2.05% and 1.59% in FF-FA and FF-FA-FC, respectively. It's also demonstrated that the contributions of feature warping and alignment are consistent with and without Siamese feature comparison. We posit that the performance improvements are owing to the preservation of the original image pattern by performing warping and alignment at the feature level.

The effect of Siamese feature comparison is reflected in the comparisons of: FF vs. FF-FC and FF-FA vs. FF-FA-FC. The ablation study shows measurable contribution of the Siamese feature comparison module. By using Siamese feature fusion, FF and FF-FA already show improvements comparing to the Vanilla DenseNet-121. By adding Siamese feature comparison to FF and FF-FA, the Youden's indexes of are further improved by 1.42% and 0.96%, respectively. The improvements are in line with our motivation and hypothesis that by maximizing/minimizing Siamese feature distances on areas with/without fractures, the network can learn features that are more sensitivity to fractures and less sensitive to other distracting factors.

The fracture localization performance of the method disclosed in the present disclosure is also assessed. Since the model produces detection probability map as fracture localization, standard object detection metrics do not apply. We are most interested in the percentage of fracture sites detected when the image-level false positive rate is less than 0.1. Therefore, classifier operating point value c associated with 10% false positive rate is selected, and the percentage of fractures with detection probability value higher than c, referred to as Recall@0.9, is measured. Table 3 summarizes the fracture localization results for a base-line algorithm according to Liu, in which Siamese feature distance is used as fracture predictor, the vanilla DenseNet-121 without considering symmetry, and the AASN method. The method provided by Liu was originally introduced to analyze brain MRIs, where the image/shape asymmetry has stronger correlation with abnormality. It is clear from Table 3 that AASN achieves the best fracture site recall among all evaluated methods, resulting in 86.53%. It out-performs baseline methods by substantial margins.

The base-line method according to Liu results in lowest recall, because image asymmetry indicated by the large Siamese feature distance may be caused by other imaging factors than fractures. The AASN method provided by the present disclosure offers significant improvement compared to both Liu and the vanilla DenseNet-121 method. This is due to the a plurality of features used in the AASN method, including one or more of: 1) employing Siamese feature fusion effectively exploiting symmetrical information to facilitate abnormality detection; 2) performing warping and alignment at the feature level for Siamese feature fusion leading to substantial performance gain; and 3) using feature comparison enabling the Siamese encoder to learn more sensible embedding, leading to further performance improvement.

TABLE 3

Evaluation of fracture localization performance by fracture site recall when the image-level classifier operates at 90% specificity.

| Method | Recall@0.9 |
|---|---|
| Liu | 59.95% |
| Vanilla | 80.88% |
| AASN | 86.53% |

The method and apparatus provided by the present disclosure according to the embodiments are described in detail above. The principles and implementation manners provided by the present disclosure are described herein by using specific examples. The description of the above embodiments is only used to help understand the method provided by the present disclosure. At the same time, a person skilled in the art will make changes the specific embodiments and the application scope according to the idea provided by the present disclosure. In summary, the contents of the present specification should not be construed as limiting the present disclosure.

The present disclosure contains material that is subject to copyright protection. The copyright is the property of the copyright holder. The copyright holder has no objection to the reproduction of patent documents or patent disclosure in the official records and files of the Patent and Trademark Office.

What is claimed is:

1. A method for performing computer-aided diagnosis (CAD) based on a medical scan image, comprising:
pre-processing the medical scan image to produce an input image, a flipped image, and a spatial alignment transformation corresponding to the input image and the flipped image; performing Siamese encoding on the input image to produce an encoded input feature map; performing Siamese encoding on the flipped image to produce an encoded flipped feature map;

performing a feature alignment using the spatial alignment transformation on the encoded flipped feature map to produce an encoded symmetric feature map;

performing fusion on the encoded input feature map and the encoded symmetric feature map to produce an encoded joint feature map; and performing decoding on the encoded joint feature map to produce a detection probability map of the anatomical abnormalities;

and processing the encoded input feature map and the encoded symmetric feature map to generate a diagnostic result indicating presence and locations of anatomical abnormalities in the medical scan image.

2. The method according to claim 1, wherein pre-processing the medical scan image comprises:

detecting a plurality of landmarks in the medical scan image, the plurality of landmarks including one or more pairs of bilateral symmetric landmarks;

identifying an axis of bilateral symmetry from the plurality of landmarks;

generating the flipped image as a mirror image of the input image with respect to the axis of bilateral symmetry; and generating the spatial alignment transformation that maps the flipped image to the input image to align the plurality of landmarks.

3. The method according to claim 2, wherein pre-processing the medical scan image further comprises:

extracting region of interests from the input image, the flipped image, and the spatial alignment transformation.

4. The method according to claim 1, wherein: performing fusion on the encoded input feature map and the encoded symmetric feature map includes performing a concatenation operation on the encoded input feature map and the encoded symmetric feature map.

5. The method according to claim 4, wherein:

the concatenation operation is performed within a transition module after a rectified linear unit (Relu) operation.

6. The method according to claim 1, wherein processing the encoded input feature map and the encoded symmetric feature map further comprises: performing a Siamese feature comparison on the encoded input feature map and the encoded symmetric feature map to produce a feature distance map charactering abnormality-causing feature asymmetries.

7. The method according to claim 6, wherein performing a Siamese feature comparison comprises:

performing a dimension reduction on the encoded input feature map and the encoded symmetric feature map; and calculating pixel-wise contrastive loss between the encoded input feature map and the encoded symmetric feature map as L2 distance.

8. The method according to claim 7, wherein performing the dimension reduction comprises:

projecting the encoded input feature map and the encoded symmetric feature map from a 1024-dimensional space to a 64-dimensional space.

9. The method according to claim 1, further comprising:

receiving a set of training images;

pre-processing the training images to produce point-annotated ground-truth images; and performing training of a Siamese neural network based on the training images and the point-annotated ground-truth images.

10. The method according to claim 9, wherein performing training of the Siamese neural network includes:

for a point-annotated ground-truth image containing one or more annotation points, transforming each annotation point to a binary regional mask to produce a ground-truth mask;

performing multi-scale feature fusion on a corresponding training image using a feature pyramid network to generate a predicted probability map; and calculating a Binary Cross-Entropy loss of predicted probability map against the ground truth mask.

11. The method according to claim 1, wherein:

the method is implemented by a fully convolutional Siamese network including a plurality of dense blocks, the plurality of dense blocks being split into an encoding portion and a decoding portion at a middle level after a third dense block.

12. The method according to claim 1, wherein the medical scan image is a pelvic X-ray (PXR) image and the diagnostic result includes presence and locations of pelvic fractures in the PXR image.

13. A device for performing computer-aided diagnosis (CAD) based on a medical scan image, comprising: a memory, storing computer-executable instructions; and a processor, coupled with the memory and, when the computer-executable instructions being executed, configured to: pre-process the medical scan image to produce an input image, a flipped image, and a spatial alignment transformation corresponding to the input image and the flipped image; perform Siamese encoding on the input image to produce an encoded input feature map; perform Siamese encoding on the flipped image to produce an encoded flipped feature map; perform a feature alignment using the spatial alignment transformation on the encoded flipped feature map to produce an encoded symmetric feature map;

perform fusion on the encoded input feature map and the encoded symmetric feature map to produce an encoded joint feature map; and perform Siamese decoding on the encoded joint feature map to produce a detection probability map of the anatomical abnormalities;

and process the encoded input feature map and the encoded symmetric feature map to generate a diagnostic result indicating presence and locations of anatomical abnormalities in the medical scan image.

14. The device according to claim 13, wherein the processor is further configured to: perform a Siamese feature comparison on the encoded input feature map and the encoded symmetric feature map to produce a feature distance map characterizing abnormality-causing feature asymmetries.

15. The device according to claim 14, wherein the processor is further configured to:

combine the detection probability map and the feature distance map to generate diagnostic result.

16. A non-transitory computer-readable storage medium storing a plurality of instructions, wherein when the plurality of instructions are executed by a processor, cause the processor to: pre-process a pelvic X-ray (PXR) image to produce an input image, a flipped image, and a spatial alignment transformation corresponding to the input image and the flipped image;

perform Siamese encoding on the input image to produce an encoded input feature map; perform Siamese encoding on the flipped image to produce an encoded flipped feature map; perform a feature alignment using the spatial alignment transformation on the encoded flipped feature map to produce an encoded symmetric feature map;

perform fusion on the encoded input feature map and the encoded symmetric feature map to produce an encoded joint feature map; and perform Siamese decoding on the encoded joint feature map to produce a detection probability map of the pelvic fractures;

and process the encoded input feature map and the encoded symmetric feature map to generate a diagnostic result indicating presence and locations of pelvic fractures in P×R image.

17. The non-transient computer-readable storage medium according to claim 16, wherein the plurality of instructions further cause the processor to:

perform a Siamese feature comparison on the encoded input feature map and the encoded symmetric feature map to produce a feature distance map charactering abnormality-causing feature asymmetries.

\* \* \* \* \*